(12) United States Patent
Thudor et al.

(10) Patent No.: US 7,106,955 B2
(45) Date of Patent: Sep. 12, 2006

(54) HUMIDITY CONTROLLER

(75) Inventors: Mohammad Thudor, Auckland (NZ); Stephen William McPhee, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 99 days.

(21) Appl. No.: 10/001,596

(22) Filed: Oct. 19, 2001

(65) Prior Publication Data

US 2002/0112725 A1   Aug. 22, 2002

Related U.S. Application Data

(63) Continuation-in-part of application No. 09/959,226, filed as application No. PCT/NZ00/00156 on Aug. 9, 2000, now abandoned.

(30) Foreign Application Priority Data

Aug. 23, 1999  (NZ) .................................. 337382
Oct. 19, 2000  (NZ) .................................. 507663

(51) Int. Cl.
  *A61H 33/06*   (2006.01)
  *A61M 15/00*   (2006.01)
(52) U.S. Cl. .................................. 392/394; 128/203.17
(58) Field of Classification Search ................ 392/394, 392/396, 397, 398, 386, 387, 403, 404; 128/203.12, 128/203.13, 203.14, 203.17, 203.18, 203.26, 128/203.27, 204.21, 204.22; 261/129, 130, 261/139
See application file for complete search history.

(56) References Cited

U.S. PATENT DOCUMENTS

| | | | | |
|---|---|---|---|---|
| 3,789,190 A * | 1/1974 | Orosy et al. | ................. | 219/497 |
| 4,332,165 A * | 6/1982 | Kawai et al. | ............. | 73/204.16 |
| 4,708,831 A * | 11/1987 | Elsworth et al. | ............ | 261/130 |
| 5,031,612 A | 7/1991 | Clementi | | |
| 5,349,946 A * | 9/1994 | McComb | ................ | 128/203.17 |
| 5,546,933 A * | 8/1996 | Rapoport et al. | ....... | 128/204.23 |
| 5,558,084 A | 9/1996 | Daniell et al. | | |
| 5,640,951 A | 6/1997 | Huddart et al. | | |
| 6,050,260 A * | 4/2000 | Daniell et al. | ......... | 128/204.22 |
| 6,204,623 B1 * | 3/2001 | Levy et al. | ................. | 318/641 |
| 6,349,722 B1 * | 2/2002 | Gradon et al. | ......... | 128/203.17 |

FOREIGN PATENT DOCUMENTS

| | | |
|---|---|---|
| AU | 1486395 | 9/1995 |
| EP | 885623 A2 | 12/1998 |
| GB | 1294808 | 11/1972 |
| GB | 2192136 | 1/1988 |
| GB | 2338420 | 12/1999 |
| JP | 5317428 | 12/1993 |

* cited by examiner

*Primary Examiner*—Sang Paik
(74) *Attorney, Agent, or Firm*—Trexler, Bushnell, Giangiorgi, Blackstone & Marr, Ltd.

(57) ABSTRACT

A breathing assistance apparatus adapted to deliver humidified gases at a desired level of humidity to a patient including a humidifier and a heated conduit is disclosed. The humidifier includes a controller which determines the flow rate of the gases and then determines the required power input to the humidifier to deliver the gases to the patient at the required patient humidity. This means the need for external sensors is dispensed with and thus the apparatus is simple and less bulky. The resistance of the conduit heater element is monitored to give a coarse indication of flow rate.

16 Claims, 8 Drawing Sheets

HUMIDITY CONTROLLER

This application is a continuation-in-part of U.S. patent application Ser. No. 09/959,226, filed on Oct. 18, 2001 now abandoned and accorded filing of Jan. 23, 2002 under 35 U.S.C. §371 and entitled "Humidity Controller", which is the United States National Phase application of PCT patent application No. PCT/NZ00/00156 which has an international filing date of Aug. 9, 2000, and was published by the International Bureau in English on Mar. 1, 2001 under International Publication Number WO 01/13981 A1.

TECHNICAL FIELD

This invention relates to breathing assistance apparatus, particularly but not solely, for supplying optimal humidity temperature of gases to a patient to assist the patient's breathing.

BACKGROUND ART

A number of methods are known in the art for assisting a patient's breathing. Continuous Positive Airway pressure or CPAP involves the administration of air under pressure to a patient, usually by a nasal mask. It is used in the treatment of snoring and Obstructive Sleep Apnea (OSA), a condition characterised by repetitive collapse of the upper airway during inspiration. Positive pressure splints the upper airway open, preventing its collapse. Treatment of OSA with nasal CPAP has proven to be both effective and safe, but CPAP is difficult to use and the majority of patients experience significant side effects, particularly in the early stages of treatment.

Upper airway symptoms adversely affect treatment with CPAP. Mucosal drying is uncomfortable and may awaken patients during the night. Rebound nasal congestion commonly occurs during the following day, simulating a viral infection. If untreated, upper airway symptoms adversely affect rates of CPAP use.

Increases in nasal resistance may affect the level of CPAP treatment delivered to the pharynx, and reduce the effectiveness of treatment An individual pressure is determined for each patient using CPAP and this pressure is set at the mask. Changes in nasal resistance affect pressure delivered to the pharynx and if the changes are of sufficient magnitude there may be recurrence of snoring or airway collapse.

Such symptoms can also occur in a hospital environment where a patient is on a respirator. Typically in such situations the patient is intubated. Therefore the throat tissue may become irritated and inflamed causing both distress to the patient and possible further respiratory problems.

A number of methods may be employed to treat such upper airway symptoms, including pharmacologic agents to reduce nasal disease, or heating the bedroom. One most commonly employed method is humidification of the inspired air using an in line humidifier. Two types of humidifier are currently used. Cold passover humidifiers rely on humidifying the air through exposure to a large surface area of water. While they are cheap, the humidity output is low at high flows, typically 2 to 4 mg/L absolute humidity at flows above 25 L/min. The output is insufficient to prevent mucosal drying. Heated water bath humidifiers are more efficient, and produce high levels of humidity even at high flow rates. They are effective at preventing upper airway mucosal drying, prevent increases in nasal resistance, and are the most reliable means of treating upper airway symptoms.

Any of these active systems will have, to some degree or other, condensation (or rain out) in the tubing connecting the humidifier to the patient. The degree of condensation is strongly dependent on the ambient temperature, being much greater for greater differences between the ambient temperature and the gas temperature. The formation of large quantities of water in the breathing tubing causes considerable inconvenience to the patient, may accelerate cooling of the gas, may eventually occlude the tubing, or may be expelled into the patient Also, the patient may experience discomfort, when breathing gases are delivered at temperatures widely divergent from that of the ambient temperature. Excessive condensation also results in inefficient usage of the water in the humidifying chamber.

In a hospital environment, where the ambient temperature of the atmosphere within the hospital environment is controlled by air conditioning for example, the required temperature for the humidified gases supplied by the apparatus may be controlled within set temperature parameters that are sufficiently close to the ambient temperature to prevent condensation within the conduit. However it is still necessary to have good control over the temperature and humidity of gases as they are actually supplied to the patient.

In the home care environment in which a user requires to use humidifying apparatus at home, the range of ambient and gas temperatures may well exceed that of the hospital environment. In the home care environment, the user will usually wear a face mask which is connected to end of the conduit and such a humidifier may be used in the home environment for the treatment of breathing and sleep apnea disorders and/or in conjunction with ventilators or CPAP devices. In addition, non active humidifiers are commonly employed utilising the known pass over humidification technique.

In U.S. Pat. No. 5,640,951 issued to Fisher and Paykel a heated conduit for a humidified breathing assistance apparatus is disclosed which includes a temperature probe at the end of a heated conduit. By heating the conduit the problems relating to condensation in the conduit may be overcome. However in order to implement closed loop control over the temperature of the supplied gases (and therefore the power input to the conduit heater element), it is necessary to measure the temperature as close to the point at which it is supplied as possible. The temperature probe and its associated wiring included for this purpose make the attachment to the face mask or intubated patient bulky and therefore more uncomfortable for the patient. Therefore it would be advantageous if a heated conduit for a humidified breathing assistance apparatus could be implemented without the need for a temperature probe at the end of the conduit. It would also be advantageous to have some indication of when the flow rates changes to any significant extent This would be useful to avoid thermal overshoot in the gases supplied to the patient, to avoid any danger of buns to the respiratory tract.

DISCLOSURE OF THE INVENTION

It is an object of the present invention to provide a breathing assistance apparatus which goes some way to overcoming the above mentioned disadvantages or which at least provides the public or industry with a useful choice.

Accordingly in a first aspect the invention consists in a breathing assistance apparatus adapted to deliver humidified gas at a desired level of humidity or at a desired temperature to a patient using open loop control comprising:

a humidifier having an electrical input power and capable of humidifying said gas up to a level of humidity prior to delivery to said patient, said level of humidity depending on said input power to said humidifier, and a controller or processor configured or programmed to:
(a) determine a parameter relating to the flow rate of said gas through said apparatus;
(b) determine based on at least said parameter the required electrical power input to said humidifier to deliver said gas to said patient at a level of humidity or at a temperature substantially similar to said desired level of humidity or said desired temperature;
(c) supply as said input power to said humidifier a level of power substantially similar to said determined power input to said humidifier;
(d) continuously monitor said parameter, and when a change in said parameter is greater than a first threshold, indicating a change in the flow rate of said gas, said controller or processor reverts to said instruction (a).

Preferably when a change in said parameter is greater than a second threshold indicating said controller or processor reverts to instruction (b), said second threshold relating to a lesser change in the flow rate than said first threshold.

Preferably said breathing assistance apparatus further comprises:
a conduit configured to convey said humidified gas from said humidifier to a patient,
a conduit heater having an electrical input power, and being associated with said conduit wherein the gas flowing through said conduit are heated either directly or indirectly by said conduit heater whereby the level of heating depending on said input power to said conduit heater;
an ambient temperature sensor providing an indication of the exterior temperature or said controller or processor storing an assumption of the exterior temperature used as an in indication of the exterior temperature; and said instruction (b) further comprises determining based on at least said indication of the exterior temperature the required power input to said conduit heater to deliver said gas to said patient at a level of humidity or at a temperature substantially similar to said desired level of humidity or said desired temperature;
and said instruction (c) further comprises supplying as said input power to said conduit heater a level of power substantially similar to said determined power input to said conduit heater.

Preferably said first threshold relates to the rate of change of said parameter with respect to time, wherein when said rate of change is greater than said first threshold said controller or processor reverts to said instruction (a).

Preferably if said rate of change or said change in said parameter indicates a decrease in flow said controller or processor pauses for a first delay before said controller or processor reverts to said instruction (a) and if said rate of change or said change indicates an increase in flow said controller or processor pauses for a second delay before said control means controller or processor reverts to said instruction (a), said second delay being longer than said first delay.

Preferably said controller or processor monitors said input power supplied to said conduit heater to provide an indication of the resistance or temperature of said conduit heater.

Preferably said indication of the temperature or resistance is used by said controller or processor at least in said instruction (d) as said parameter relating to the flow rate of said gas.

Preferably said input power to said conduit heater comprises a voltage signal and a current signal, and said indication of the temperature or resistance relates at least in part to said voltage signal and/or said current signal and said input power to said conduit heater.

Preferably said humidifier comprises a humidification chamber adapted to receive a volume of water and water heater to heat said water to produce water vapour within said chamber in use, said gas passing through said water vapour in said chamber thereby being humidified, said instruction (a) further comprising:
i) energising said water heater to heat said water towards a first condition,
ii) continuously monitoring said parameter or a variable indicative of a property of said water heater, until said variable or said parameter indicates that said water has substantially reached said first condition,
iii) determining said parameter based on at least said variable and said indication of the external temperature.

Preferably the determination of said power to said humidifier in said instruction (b) is also based on said indication of the external temperature.

Preferably said breathing assistance apparatus further comprises a gas supply means adapted to supply gas to said humidifier at a required pressure and resulting flow rate.

Preferably said gas supply provides an output signal representative the level of electrical output to said gas supply, said signal being supplied to said controller or processor from which the flow rate of said humidified gas is determined.

Preferably said gas supply comprise a fan driven by a variable speed electric motor.

Preferably said parameter is based on the current drawn by said variable speed motor.

Preferably said breathing assistance apparatus further comprises a gas flow rate sensor from which said parameter is determined directly.

Preferably said humidifier further comprises:
a chamber sensor providing an indication of the temperature of said water heater and providing an indication of the electrical power drawn by said water heater,
wherein said variable is indicative of said indicator of the temperature of said water heater or said indication of the power drawn by said water heater.

Preferably said parameter at least in said instructions (a), (b) and (c) is defined as the value of said power drawn by said water heater divided by said temperature of said water heater.

In a second aspect a method of delivering humidified gas at a desired level of humidity or at a desired temperature to a patient using an open loop controlled humidifier comprising the steps of:
(a) determining a parameter relating to the flow rate of said gas through said humidifier;
(b) determining based on at least said parameter the required electrical power to said humidifier to deliver said gas to said patient at a level of humidity or at a temperature substantially similar to said desired level of humidity or said desired temperature;
(c) supplying a level of power to said humidifier substantially similar to said determined power;
(d) continuously monitoring said parameter, and when a change in said parameter is greater than a first threshold, indicating a change in the flow rate of said gas, revert to step (a).

Preferably said method further comprising: when a change in said parameter is greater than a second threshold indicating said controller or processor reverts to instruction (b), said second threshold relating to a lesser change in the flow rate than said first threshold.

Preferably said method further comprising the steps:
conveying said humidified gas to a patient
heating the conveyed gas either directly or indirectly using a conduit heater;
sensing or making an assumption of the exterior temperature;
and said instruction (b) further comprises determining based on at least said indication of the exterior temperature the required power input to said conduit heater to deliver said gas to said patient at a level of humidity or at a temperature substantially similar to said desired level of humidity or said desired temperature;
and said instruction (c) further comprises supplying as said input power to said conduit heater a level of power substantially similar to said determined power input to said conduit heater.

Preferably said first threshold relates to the rate of change of said parameter with respect to time, wherein when said rate of change is greater than said first threshold said controller or processor reverts to said instruction (a).

Preferably said rate of change or said change in said parameter indicates a decrease in flow said controller or processor pauses for a first delay before said controller or processor reverts to step (a) and if said rate of change or said change indicates an increase in flow said controller or processor pauses for a second delay before said controller or processor reverts to step (a), said second delay being longer than said first delay.

Preferably said method further comprising the step of monitoring the input power supplied to said conduit heater to provide an indication of the resistance or temperature of said conduit heater.

Preferably said indication of the temperature or resistance is used at least in step (d) as said parameter relating to the flow rate of said gas.

Preferably said input power to said conduit heater comprises a voltage signal and a current signal, and said indication of the temperature or resistance relates at least in part to said voltage signal and/or said current signal and said input power to said conduit heater.

Preferably said humidifier comprises a humidification chamber adapted to receive a volume of water and water heater to heat said water to produce water vapour within said chamber in use, said gas passing through said water vapour in said chamber thereby being humidified, said instruction (a) further comprising:
i) energising said water heater to heat said water towards a first condition,
ii) continuously monitoring said parameter or a variable indicative of a property of said water heater, until said variable or said parameter indicates that said water has substantially reached said first condition,
iii) determining said parameter based on at least said variable and said indication of the external temperature.

Preferably the determination of said power to said humidifier in said instruction (b) is also based on said indication of the external temperature.

Preferably said method further comprising the step of supplying gas to said humidifier at a required pressure and resulting flow rate.

Preferably said method further comprising the step of determining the level of electrical power required to supply said gas at a required pressure and resulting flow rate, from which the flow rate of said humidified gas is determined.

Preferably said gas is supplied by a fan driven by a variable speed electric motor.

Preferably said parameter is based on the current drawn by said variable speed motor.

Preferably said parameter is determined directly from a gas flow rate sensor.

Preferably said method further comprising:
sensing the temperature of said water heater and providing an indication of the electrical power drawn by said water heater,
wherein said variable is indicative of the temperature of said water heater or said indication of the power drawn by said water heater.

Preferably said method further comprising:
sensing the temperature of said water heater and providing an indication of the electrical power drawn by said water heater,
wherein said variable is indicative of the temperature of said water heater or said indication of the power drawn by said water heater.

In a third aspect the invention consists a breathing assistance apparatus adapted to deliver humidified gas at a desired level of humidity or at a desired temperature to a patient using open loop control comprising:
humidifier having an electrical input power and capable of humidifying said gas up to a level of humidity prior to delivery to said patient, said level of humidity depending on said input power to said humidifier,
means for determining a parameter relating to the flow rate of said gas through said apparatus;
means for determining based on at least said parameter the required electrical power input to said humidifier to deliver said gas to said patient at a level of humidity or at a temperature substantially similar to said desired level of humidity or said desired temperature;
means for supplying as said input power to said humidifier a level of power substantially similar to said determined power input to said humidifier;
means for continuously monitoring said parameter, and when a change in said parameter is greater than a first threshold, indicating a change in the flow rate of said gas, the flow rate is determined again.

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting.

The invention consists in the foregoing and also envisages constructions of which the following gives examples.

BRIEF DESCRIPTION OF THE DRAWINGS

One preferred form of the present invention will now be described with reference to the accompanying drawings in which.

DETAILED DESCRIPTION OF THE INVENTION

Whether used in a hospital environment or in a home care environment, the present invention will generally have associated two main pieces of apparatus. Firstly an active humidifier which controls the temperature of a heater plate heating a body of water to achieve a desired temperature and humidity of the gases being humidified. Secondly a transport conduit from the humidifier to the patient is also required, which is preferably heated to reduce condensation, or "rain out".

Figure 1:
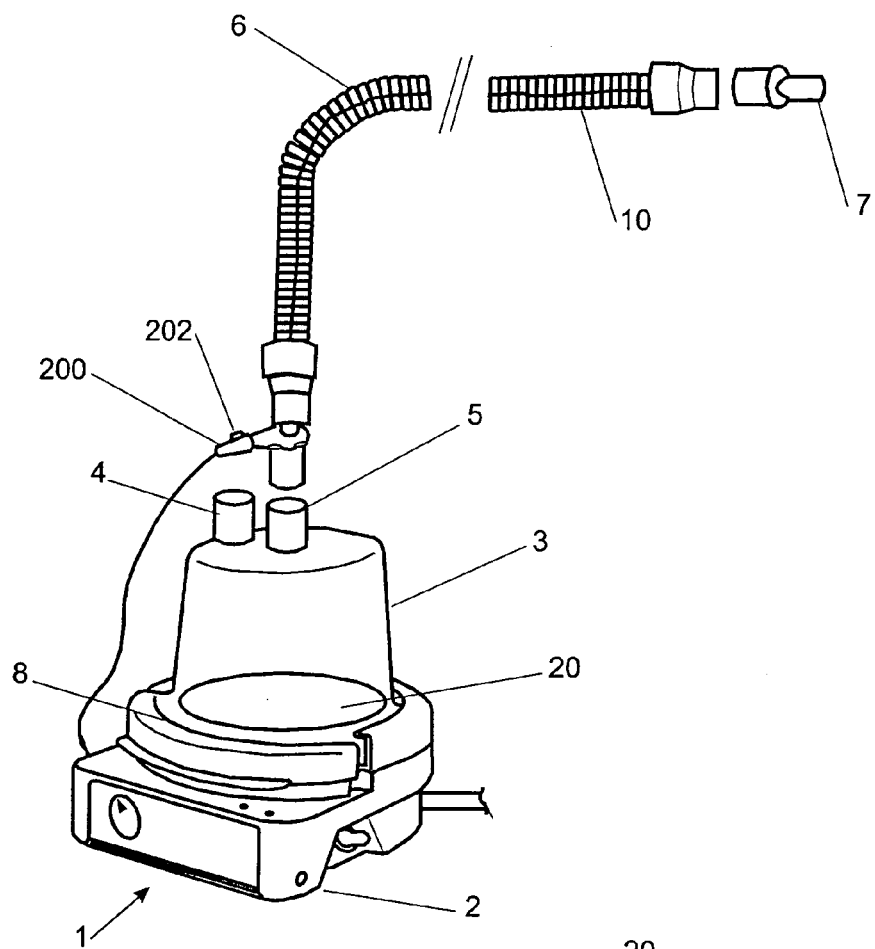
FIG. 1 is a illustration of a respiratory humidifier system.
Figure 2:
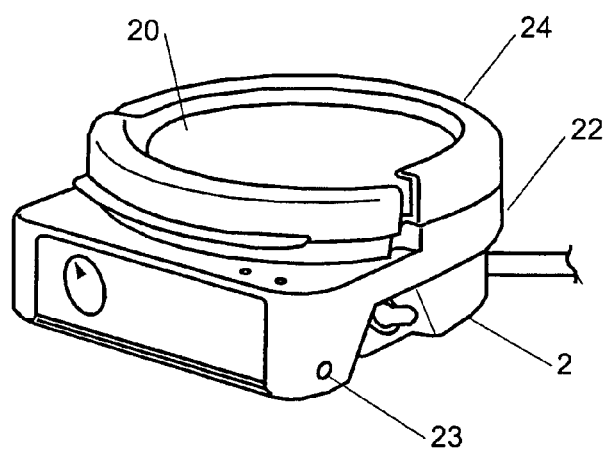
FIG. 2 is a illustration of the humidifier base of the respiratory humidifier system of FIG. 1.

Referring to FIG. 1 a humidifying apparatus as might be used in a hospital generally referenced 1 is shown. The apparatus comprises a body 2 containing heating means comprising a heating plate 20 having an electric heating element therein or in thermal contact therewith and control means for example electronic circuitry which may include a microprocessor for controlling the supply of energy to the heating element. The body 2 is removably engageable with a humidifying chamber 3 which contains water for humidifying gases. Referring to FIG. 2 which show the humidifier apparatus in more detail, the humidifying chamber 3 has edges which engage with collar 24 on the humidifier apparatus. The gases to be humidified may be a mixture of air, oxygen and anaesthetic for example which are supplied to the chamber through a gases inlet 4. This might be connected to a ventilator, or in the case of CPAP therapy a CPAP blower. A gases outlet 5 is also provided and the gases outlet 5 is connected to the conduit 6 (FIG. 1) which conveys humidified gases to a remote destination such as an intubated patient at the end 7 of the conduit. Alternatively, the end 7 of the conduit may have a gas mask attached thereto, which mask is used to cover a nose and/or mouth of a user so as to supply humidified gases to the user for breathing, as in the delivery of CPAP therapy. The humidifier heater plate 20 has a temperature transducer 8 which is in electrical connection with the electronic control circuitry in body 2 of the apparatus so that the control means monitors the temperature of the heating plate.

A heating element 10 is provided within the conduit 6 to help prevent condensation of the humidified gases within the conduit. Such condensation is due to the temperature of the walls of the conduit being close to the ambient temperature, (being the temperature of the surrounding atmosphere) which is usually lower than the temperature of the humidified gases within the conduit. The heater element is effectively replaces the energy lost from the gases through conduction and convection during transit through the conduit. Thus the conduit heater element ensures the gases delivered are at an optimal temperature and humidity.

The present invention provides a means of controlling at least the heater plate and preferably also the conduit heater element without the need for any sensors, either in the humidifier chamber or positioned in the conduit. This is achieved by estimating the rate of flow of gases through the humidifier using parameters already available to the controller. For a given humidifier an appropriate level of power can then be determined to apply to the heater plate to achieve the desired temperature of gases delivered to the patient. Additionally this may be used to provide a more appropriate level of energisation at this conduit heater element. This not only saves the cost of the extra sensors but also allows the apparatus connected to the end of the conduit to be simpler and lighter, In the preferred embodiment of the present invention the controller 100, shown in FIG. 3, uses a range of inputs to control both the power 108 supplied to the heater plate 110 as well as the power 114 supplied to the conduit heating element 116 (if present). In certain applications it may also be used to provide control instructions to auxiliary apparatus such as a blower fan. Using an internal algorithm 106 the controller 100 estimates the power 108 to supply to the humidifier heater plate 110 to achieve a given humidity and or temperature of gases at the top of the humidifier chamber alternatively (or estimates the temperature to achieve a given power). It then uses a second algorithm 102 to estimate the required power 114 to supply to the conduit heater element 116 and the humidifier heater plate 110 to achieve optimal temperature and/or humidity of the gases delivered to the patient 118.

Figure 4:
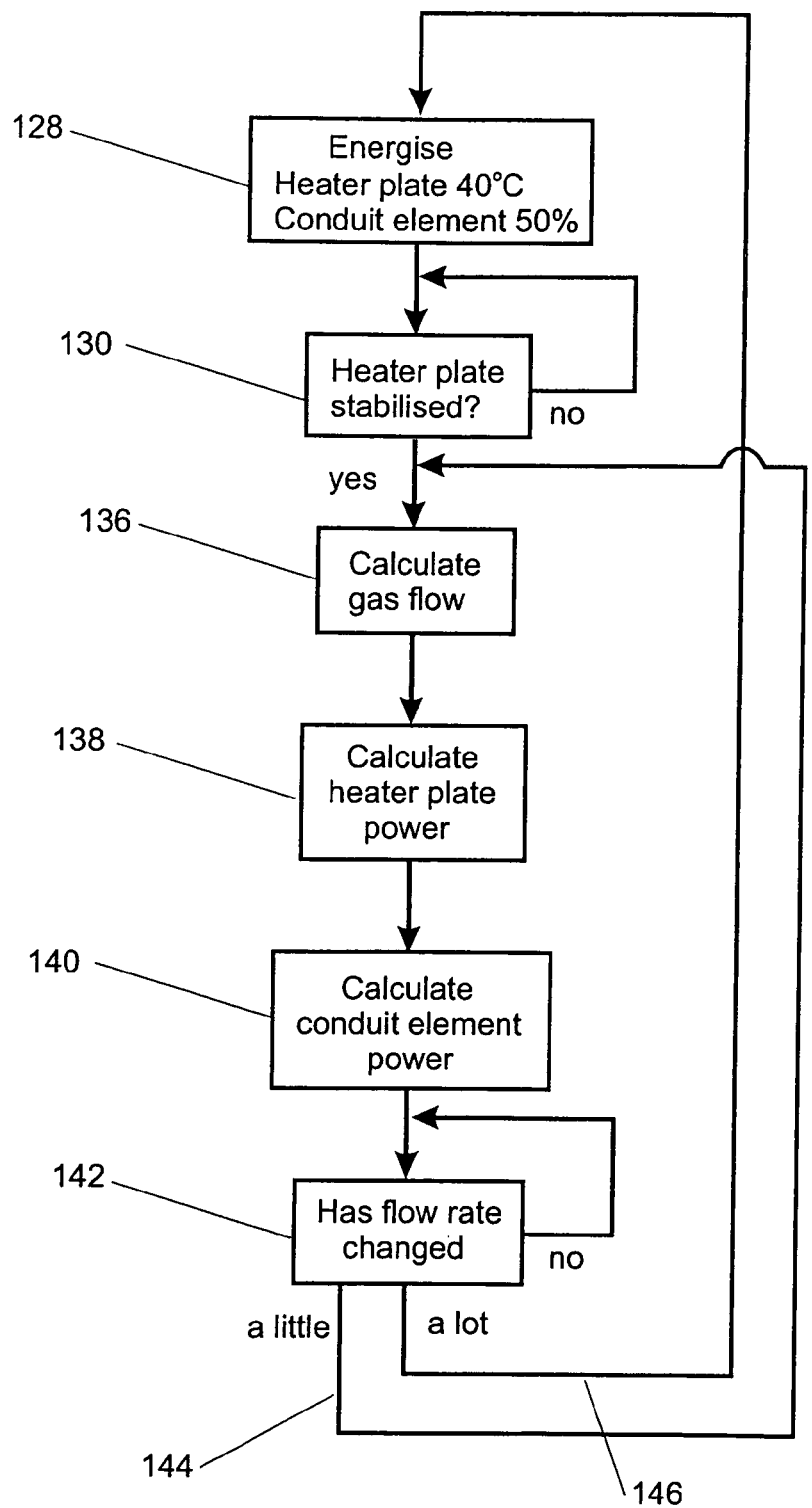
FIG. 4 is a flow diagram of the algorithm used to control the heater plate and the heater wire within the respiratory conduit.
Figure 5:
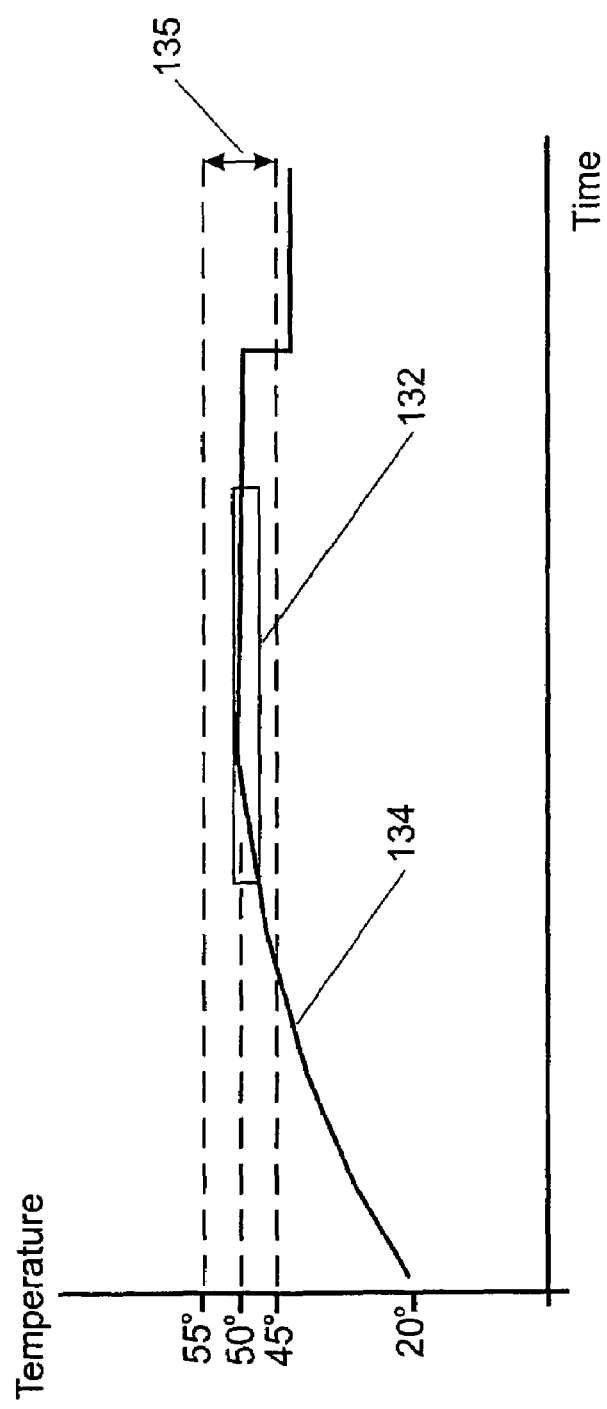
FIG. 5 is an example of how the heater plate temperature varies over time, when the pressure is controlled constant.

Referring to FIG. 4, when the humidifier starts up the controller executes a supervisory algorithm, which controls the heater plate and if present the conduit heater element. Initially 128 the heater plate is controlled to a temperature of 40° C. and the conduit heater element may be energised with a duty cycle of for example 50%. The heater plate temperature (or alternatively the power supplied to the heater plate) is then monitored 130 until it settles to a stabilised level. Effectively a window 132 is superimposed over the heater plate temperature profile 134 of which an example is shown in FIG. 5. When the profile 134 (over the entire period of the window 132) fits within the bounds of the window 132, it is effectively considered to have stabilised. Once this has occurred the controller enters a calculation stage.

Firstly, it calculates the flow rate of the gases 136 using any one of a number of methods which will be described later.

Figure 6:
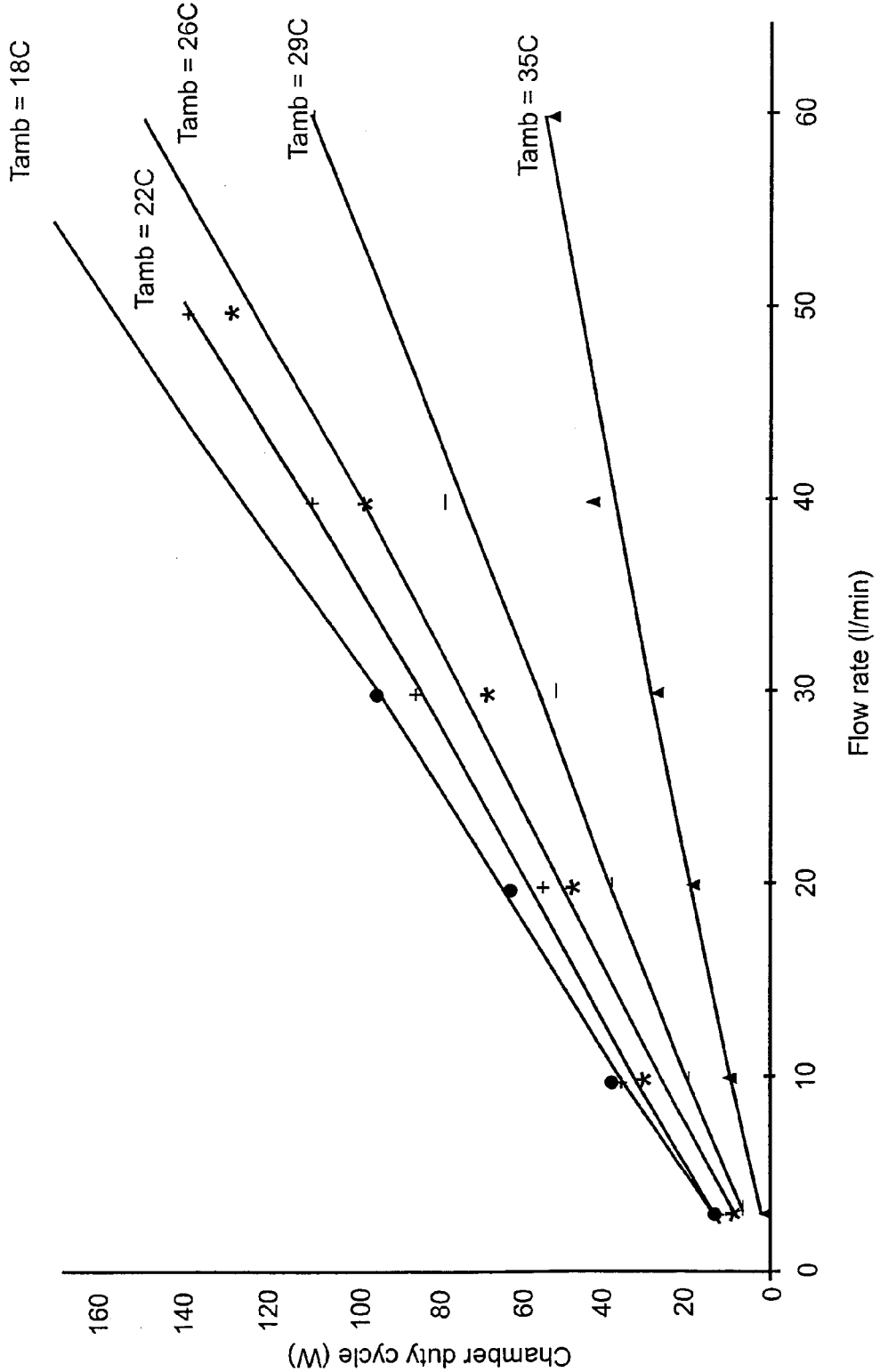
FIG. 6 is a graph of heater plate power against flow rate.

Secondly knowing the rate of flow of the gases the algorithm then calculates the required heater plate power 138 (alternatively heater plate temperature) to achieve a desired temperature/humidity of gases. A relationship has been empirically determined using a humidifier and a heated conduit such as that as described in U.S. Pat. No. 5,640,951, the contents of which are incorporated herein by reference. The actual relationship for any other arrangement would either have to be empirically determined by experimentation or theoretically calculated. For a desired temperature of gases exiting the humidifier of for example 37° C. the relationship between the power supplied to the heater plate ($P_{HP}$), the rate of flow of gases ($F_{gas}$) and the ambient temperature ($T_{amb}$) is graphed in FIG. 6. From this an approximate general algebraic equation has been extrapolated which the controller can use to determine an approximate level of power to apply to the heater plate:

$$P_{HP} = (-0.1239 \times T_{amb} + 5.383) \times F_{gas} + (-0.3112 \times T_{amb} + 10.738)$$

Figure 7:
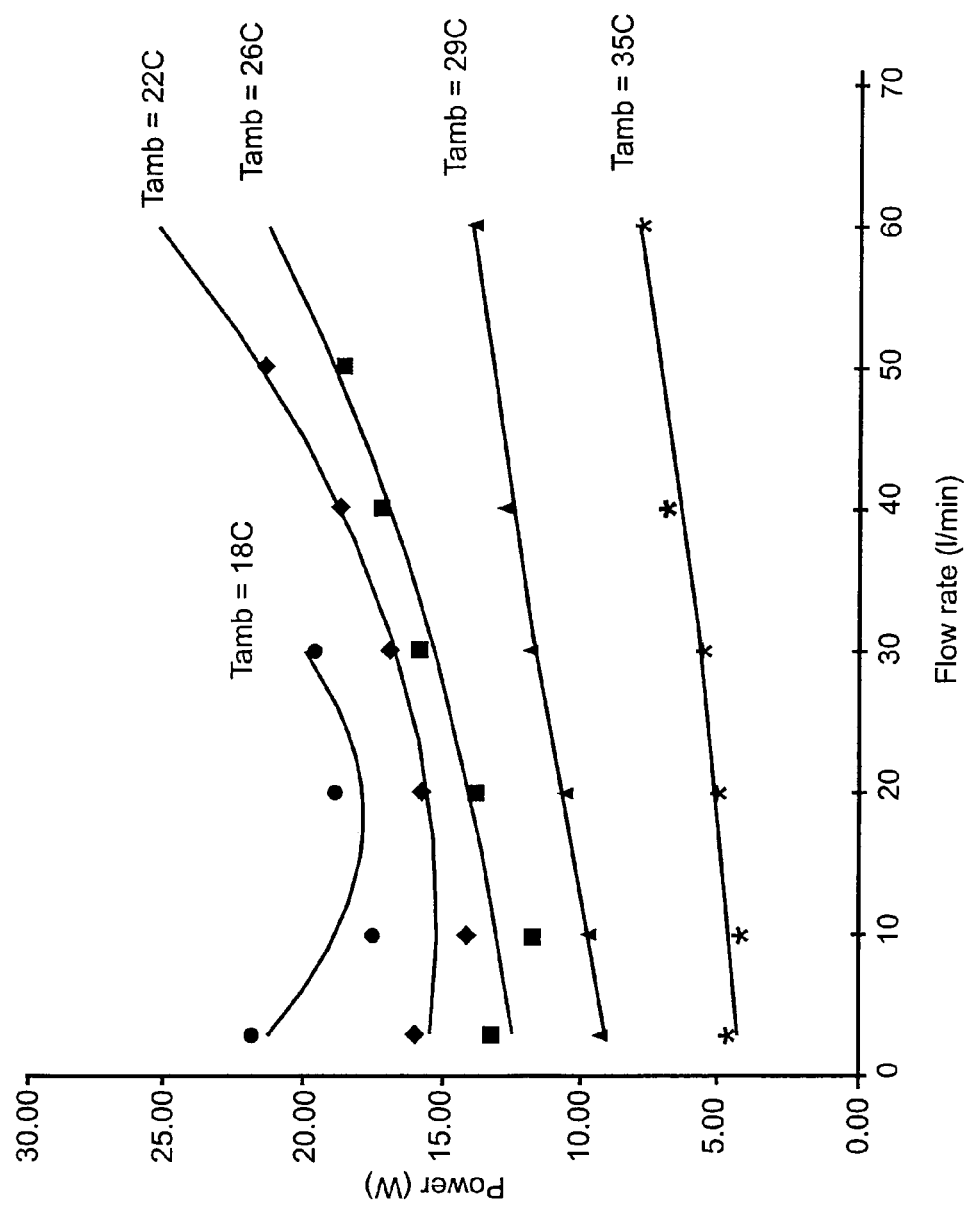
FIG. 7 is a graph of conduit heater element power and flow rate.

Thirdly the algorithm calculates the required power input to the conduit heater wire 140 to deliver a desired temperature of the gases to the patient. With gases flowing at a known rate of flow it is possible to calculate the resultant temperature of the gases once they have flowed through a conduit of known characteristics surrounded by the atmosphere at a known or assumed ambient temperature. Thermal characteristics of the conduit will either be known or can be calculated by experimentation. This relationship is based off empirical data using a humidifier and a heated conduit such as that as described in U.S. Pat. No. 5,640,951. The actual relationship for any other arrangement would either have to be empirically determined by experimentation or theoretically calculated. With a conduit entry gas temperature of 37° C. and a temperature of gases delivered to the patient of 40° C., the relationship between the flow rate of the gases ($F_{gas}$), the power input to the conduit heater element ($P_c$), the ambient temperature ($T_{amb}$) is graphed in FIG. 7. This is extrapolated to a general algebraic expression:

$$P_c=(-0.0005*T_{amb}+0.0169)F_{gas}^2-[10^{-5}*T_{amb}^3-0.0042*T_{amb}^2+0.2189*T_{amb}-3.0075]F_{gas}-1.0169*T_{amb}+38.956$$

Practically this relationship can be simplified whereby $P_c$ is dependent only on $T_{amb}$. This is an acceptable approximation for the conduit heater element, as it is not as crucial as the heater plate.

Monitoring of Flow Interruption

Once the heater plate and conduit heater element have been appropriately energised, the controller continues to monitor 142 the system for any changes in the variables. The main reason for this is to avoid thermal overshoot ie where the flow drops suddenly, the temperature of gases can become dangerously high.

In order to monitor effectively, two methods are used. Firstly the flow rate is monitored and secondly the change in flow rate (with respect to time) is also monitored. The first 144 is to allow the system to respond to any changes in the system. The second 146 is a fast response system in order to avoid thermal overshoot. Effectively where either $P_{HP}$ or $T_{HP}$ is controlled constant, monitoring the other variable gives an indication of any change in flow, or any other variable which requires a recalculation.

In order to monitor the flow a number of methods of estimating the flow are available. In the preferred embodiment of the present invention the flow is monitored for this purpose by monitoring the resistance of the heater wire 116. The resistance will change according to the temperature of the heater wire, which will in turn be dependent on the flow of gases passing through the conduit 6 and the power supplied to the conduit heater element 116. Thus for a set input power, when the flow rate of the flow of gases changes, the temperature of the conduit heater element 116 will be affected and this will be reflected in the indication of the resistance of the conduit heater element 116.

Figure 8:
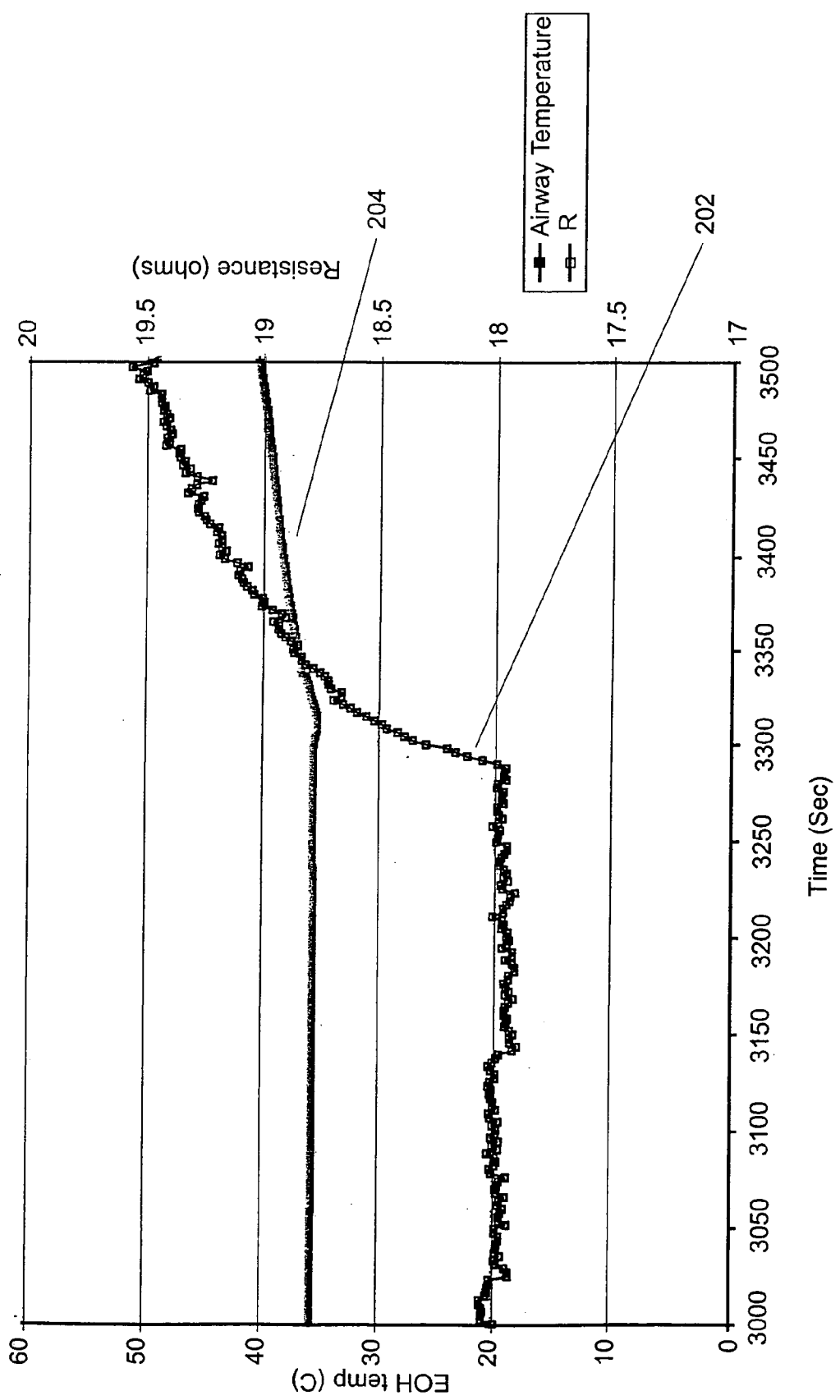
FIG. 8 is a graph of the airway temperature and the measured resistance of the heater wire versus time and for a reduction in flow from 60 l/min to 5 l/min.
Figure 9:
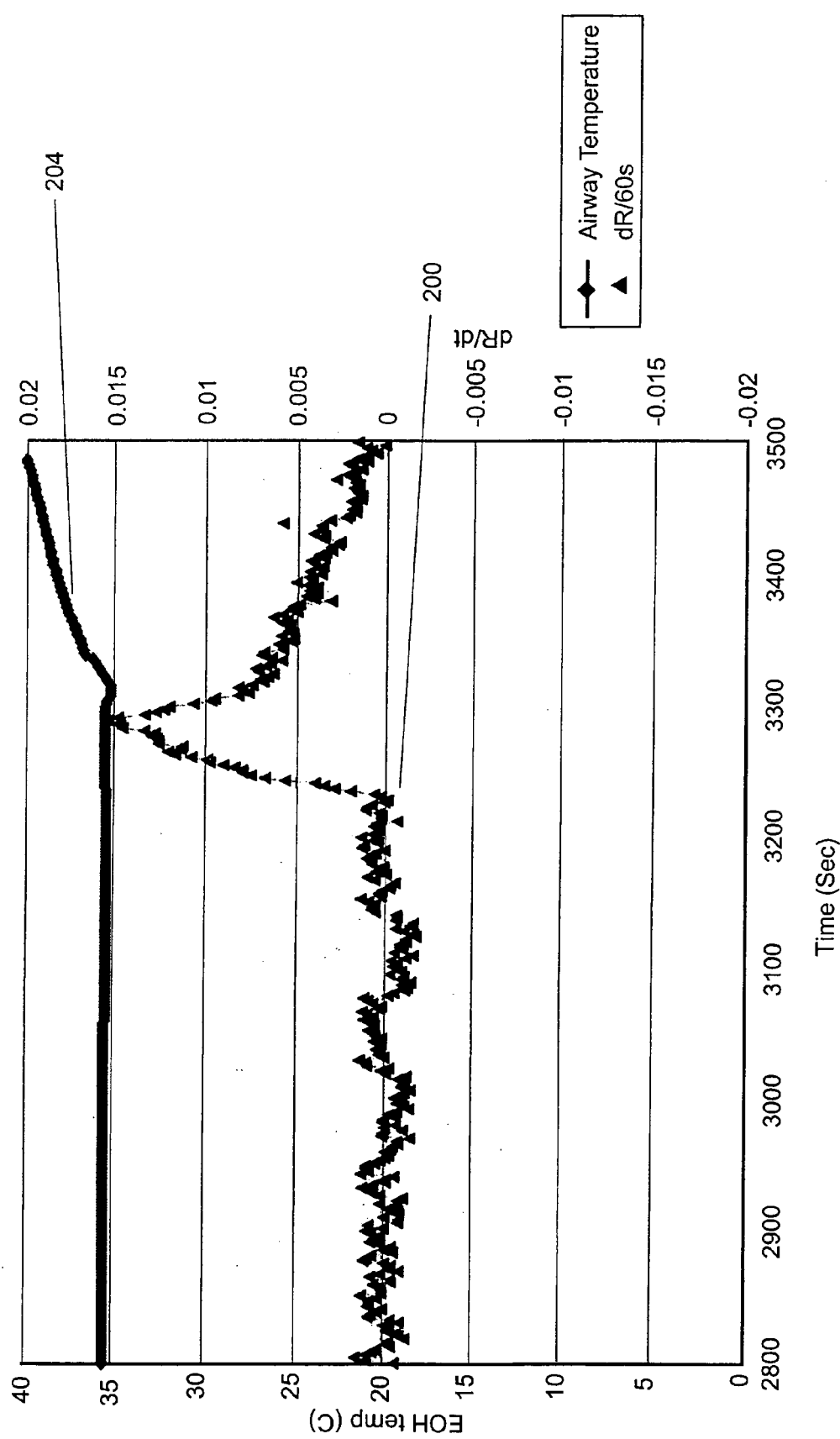
FIG. 9 is a graph of the airway temperature and the measured change in resistance with respect to time for a reduction in flow from 60 l/min to 5 l/min.

The relationship between the airway and temperature 204 resistance (R) of the heater wire 116 is shown in FIGS. 8 and 9. This indicates an almost linear relationship, which for this purpose can be considered linear. In this fashion large changes in the flow will be quickly detected by monitoring dR/dt 200; seen in FIG. 9 and more gradually detected by monitoring R 202 seen in FIG. 8.

A less preferred method is monitoring a variable x (defined as $P_{HP}/T_{HP}$), which is closely related to the flow rate, is constantly calculated and monitored. If it goes up there is a 30 minute delay before the controller initiates a recalculation, to avoid spurious readings and unnecessary calculations. If it goes down there is a 30 second delay before the controller recalculates, to avoid any possibility of the delivered gases being, even transiently, too hot.

Where large step changes occur the controller needs to react quickly. In such cases it will reset to initial conditions to wait until the system stabilises again, as any calculations in the interim would be pointless. To achieve this dx/dt is calculated and monitored. While a negative value is more dangerous, any deviation over a certain value will reset the controller.

In a further alternative embodiment of the present invention the expected heater plate temperature is calculated using $$T_{HP}=-7.3319*Ln(F_{gas})+63.655$$

and if the actual heater plate temperature deviates by more than 5° C. then the program recalculates the required powers.

Thus in summary controller carries out the following steps:

(1) Estimates the rate of flow of gases keeping all variables constant 136.

(2) Estimate the required heater plate power/temperature to achieve a specified temperature/humidity of gases in the humidification chamber 138.

(3) Calculate the power input to the heater wire to achieve a desired output temperature 140.

It will be appreciated that a greater level of power will be supplied to the conduit heater element if:

i) the rate of flow of the gases reduces, ii) the ambient temperature decreases, iii) the differential between ambient and gases temperature increases.

It will also be appreciated that the heater plate temperature could be controlled to a set valve (using closed loop control) as opposed to power. In this case the power supplied would be monitored as a measure of system stability. Furthermore where relationships are expressed algebraically they could equally be stored in look-up tables.

First Preferred Embodiment of Flow Estimation

Generally when used in a hospital setting a humidifier such as that described in the present invention will be used in conjunction with a respirator to supply humidified gases to an intubated patient, or possibly using a respiratory mask. As such the humidifier will operate effective independently of the respirator and therefore must make all of its control decisions based on only the sensors contained therein. In the preferred embodiment of the present invention the flow rate of the gases passing through the humidification chamber can first be estimated by comparing the power input required 108 for the humidifier heater plate to the measured temperature 112 of the heater plate. In effect the higher the rate of flow of gases the larger the amount of power required by the heater plate in order to achieve a given heater plate temperature. Thus for a given system the relationship between power to heater plate and flow rate for a given heater plate temperature can either be determined empirically or theoretically calculated. Again using a humidifier and a heated conduit such as that as described in U.S. Pat. No. 5,640,951 the following empirically determined relationship applies:

$$F_{gas} = \frac{-(0.831 - 0.0049 * T_{amb}) + \sqrt{abs \mid (0.831 - 0.0049 * T_{amb})^2 - (4 * (0.00004 * T_{amb} - 0.0057) * ((14.348 - 0.25 * T_{amb}) - P_{HP})) \mid}}{2 * (0.0004 * T_{amb} - 0.0057)}$$

where $P_{HP}$ is the power applied to the heater plate to achieve a given heater plate temperature in steady state of 50° C., $T_{amb}$ is the ambient temperature and $F_{gas}$ is the gas flow rate.

It will be appreciated this method is more appropriate in the hospital care environment where the ambient temperature can be assured with a high degree of confidence.

Second Preferred Embodiment of Flow Estimation

In the homecare environment the present invention will often be employed in conjunction with a continuous positive airway pressure (CPAP) device or such other breathing apparatus which will include a fan such as that described in U.S. Pat. No. 6,050,260, the contents of which are incorporated herein by reference. It will be appreciated that in such applications it may be possible to connect the controllers of the various devices together in an arrangement such that data may be readily exchanged. In such cases the rate of flow of the gases may be estimated directly from information available either from the fan or, where provided, a flow sensor.

In this embodiment of the present invention the flow is estimated based on the loading of the fan. Generally the fan will be controlled to run at a specified speed and therefore deliver a constant pressure output. The flow rate of the gases will depend on the restrictions in the flow path. In turn in order to maintain the specified speed a certain power input will be required for the fan. Therefore an algebraic relationship between the actual gas flow rate and the power input to the fan can be developed for a fan of known characteristics. This relationship may either be determined empirically by experimentation or theoretically calculated using specified motor characteristics.

Figure 3:
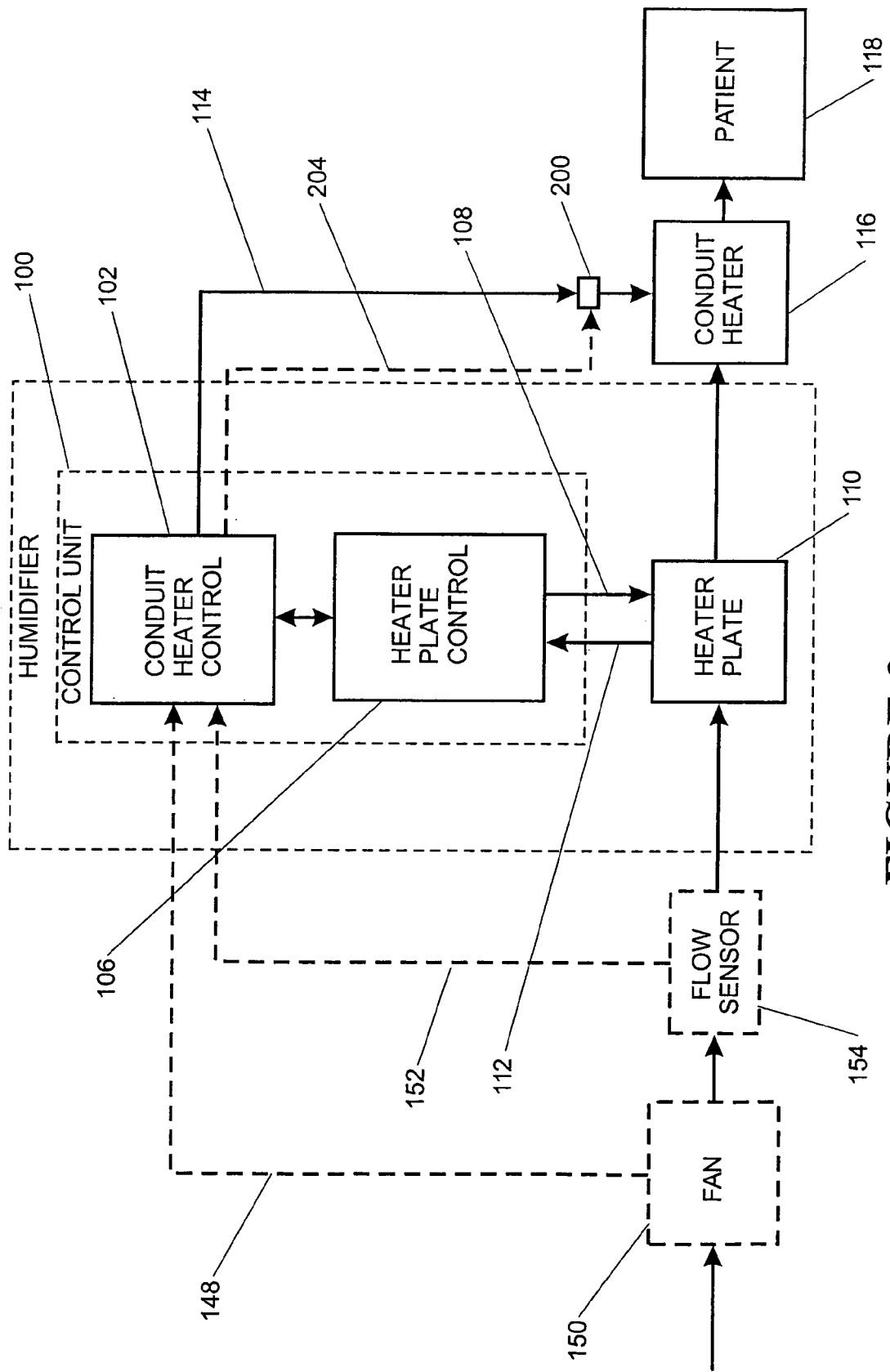
FIG. 3 is a block diagram of the control system which controls the humidifier in the preferred embodiment of the present invention.

A number of methods are known in the art for determining the loading on a motor from the supply it draws. The simplest such method would be to firstly meter the current drawn 148 from the fan 150, as indicated in FIG. 3. The current 148 is the input to the conduit heater element controller 102 where either an algebraic relationship or a look up table is used to determine the flow rate of the gases.

For example in U.S. Pat. No. 5,740,795, the contents of which are hereby incorporated herein by reference, a method is disclosed using both motor voltage and current to estimate the flow rate. While this represents one method, as mentioned above, it will be appreciated that other methods, such as based on just current, will be equally applicable.

Third Preferred Embodiment of Flow Estimation

As mentioned in the second embodiment that in certain cases a flow sensor may already be provided in the gas flow path. This being the case, the gas flow rate 152 can be extracted directly from the flow sensor 154 and used as an input to the humidifier controller 100, as indicated in FIG. 3. This is then used directly in the conduit heater element controller 102 to determine the power to apply to the heater plate 110 and conduit heater element 116 according to the algorithm shown in FIG. 4 and described earlier.

The present invention as described in the foregoing provides a novel method and apparatus for controlling the heater plate temperature in a humidifier for supplying humidified gases to a patient under respiratory therapy. This has the advantage of removing external sensors making the system simpler, cheaper and lighter. Similarly it may also allow for effective control over energisation of the conduit heater element, ensuring the system as a whole operates correctly as well as being as efficient as possible.

The invention claimed is:

1. A breathing assistance apparatus adapted to deliver humidified gas at a desired level of humidity or at a desired temperature within a conduit to a patient using open loop control comprising:
   a humidifier capable of humidifying said gas up to a level of humidity prior to delivery to said patient, the humidifier having an electrical input power, said level of humidity depending on said input power to said humidifier,
   a conduit configured to convey said humidified gas from said humidifier to a patient,
   a conduit heater associated with said conduit wherein gas flowing through said conduit is heated either directly or indirectly by said conduit heater, the conduit heater having an electrical input power, the level of heating depending on said input power to said conduit heater,
   a conduit heater power monitor providing an output indicative of the input power to said conduit heater, and
   a controller or processor configured or programmed to carry out the following instructions:
   (a) monitor said input power supplied to said conduit heater and to determine a parameter which in combination with said input power is indicative of the flow rate of gas through said conduit;
   (b) determine based on said parameter the required electrical power input to said humidifier to deliver gas to said patient at a level of humidity or at a temperature substantially similar to said desired level of humidity or said desired temperature;
   (c) supply as said input power to said humidifier a level of power substantially similar to said determined power input to said humidifier;
   (d) continuously monitor said parameter, and when a change in said parameter is greater than a first threshold, reverts to said instruction (a).

2. A breathing assistance apparatus as claimed in claim 1, wherein at instruction (d) when a change in said parameter is greater than a second threshold, said controller or processor reverts to instruction (b), said second threshold relating to a lesser change in the flow rate than said first threshold.

3. A breathing assistance apparatus as claimed in claim 1 or 2 wherein said breathing assistance apparatus further comprises:
   an ambient temperature sensor providing an indication of the exterior temperature or said controller or processor storing an assumption of the exterior temperature used as an in indication of the exterior temperature; and said instruction (b) further comprises determining based on at least said indication of the exterior temperature the required power input to said conduit heater to deliver said gas to said patient at a level of humidity or at a temperature substantially similar to said desired level of humidity or said desired temperature; and said instruction (c) further comprises supplying as said input power to said conduit heater a level of power substantially similar to said determined power input to said conduit heater.

4. A breathing assistance apparatus as claimed in claim 3 wherein said first threshold relates to the rate of change of said parameter with respect to time, wherein when said rate of change is greater than said first threshold said controller or processor reverts to said instruction (a).

5. A breathing assistance apparatus as claimed in claim 4 wherein said rate of change or said change in said parameter indicates a decrease in flow said controller or processor pauses for a first delay before said controller or processor reverts to said instruction (a) and if said rate of change or said change indicates an increase in flow said controller or processor pauses for a second delay before said controller or processor reverts to said instruction (a), said second delay being longer than said first delay.

6. A breathing assistance apparatus as claimed in claim 1, configured to estimate the temperature of said conduit heater based on the resistance of said conduit heater and at least one characteristic of said conduit heater.

7. A breathing assistance apparatus as claimed in claim 6, wherein temperature of the conduit heater or resistance is used by said controller or processor at least in said instruction (d) as said parameter relating to the flow rate of said gas.

8. A method of delivering humidified gas at a desired level of humidity or at a desired temperature to a patient using an open loop controlled humidifier comprising the steps of:
    (a) monitoring power input to a conduit heater;
    (b) determining a parameter which in combination with said power input is indicative of the flow rate of said gas through said conduit heater;
    (c) determining based on at least said parameter the required electrical power to said humidifier to deliver said gas to said patient at a level of humidity or at a temperature substantially similar to said desired level of humidity or said desired temperature;
    (d) supplying a level of power to said humidifier substantially similar to said determined power;
    (e) continuously monitoring said parameter, and when a change in said parameter is greater than a first threshold, indicating a change in the flow rate of said gas, revert to step (a).

9. A method as claimed in claim 8 wherein at step (e) when a change in said parameter is greater than a second threshold indicating said controller or processor reverts to step (c), said second threshold relating to a lesser change in the flow rate than said first threshold.

10. A method as claimed in claim 8 or 9 further comprising the steps of:
    conveying said humidified gas to a patient via a conduit;
    heating the conveyed gas either directly or indirectly using the conduit heater;
    sensing or making an assumption of the exterior temperature;
    at said step (c) determining based on at least said indication of the exterior temperature the required power input to said conduit heater to deliver said gas to said patient at a level of humidity or at a temperature substantially similar to said desired level of humidity or said desired temperature;
    and at said step (d) supplying as said input power to said conduit heater a level of power substantially similar to said determined power input to said conduit heater.

11. A method as claimed in claim 10 wherein said first threshold relates to the rate of change of said parameter with respect to time.

12. A method as claimed in claim 11 wherein said rate of change or said change in said parameter indicates a decrease in flow said controller or processor pauses for a first delay before said controller or processor reverts to step (b) and if said rate of change or said change indicates an increase in flow said controller or processor pauses for a second delay before said controller or processor reverts to step (b), said second delay being longer than said first delay.

13. A method as claimed in claim 8 wherein said indication of the temperature or resistance of the conduit heater is used at least in step (e) as said parameter relating to the flow rate of said gas.

14. A method as claimed in claim 10 wherein the determination of said power to said humidifier in said step (c) is also based on said indication of the external temperature.

15. A method as claimed in claim 8 further comprising the step of supplying gas to said humidifier at a required pressure and resulting flow rate.

16. A breathing assistance apparatus adapted to deliver humidified gas at a desired level of humidity or at a desired temperature to a patient using open loop control comprising:
    humidifier means having an electrical input power for humidifying said gas up to a level of humidity prior to delivery to said patient, said level of humidity depending on said electrical input power to said humidifier means,
    conduit means for conveying said humidified gas from the humidifier means to the patient,
    conduit heating means having an electrical input power, and being associated with said conduit means, wherein the gas flowing through said conduit means is heated either directly or indirectly by said conduit heating means, whereby the level of heating depends on said electrical input power to said conduit heating means, and
    means for monitoring the electrical input power to said conduit heating means and determining a parameter which in combination with said power to said conduit heating means indicative of the flow rate of said gas through said apparatus;
    means for determining based on at least said parameter the required electrical power input to said humidifier means to deliver said gas to said patient at a level of humidity or at a temperature substantially similar to said desired level of humidity or said desired temperature;
    means for supplying as said input power to said humidifier means a level of power substantially similar to said determined power input to said humidifier means;
    means for continuously monitoring said parameter, and when a change in said parameter is greater than a first threshold, indicating a change in the flow rate of said gas, the flow rate is determined again.

* * * * *